United States Patent [19]

Stearns

[11] 4,300,393
[45] Nov. 17, 1981

[54] SAMPLE INTRODUCTION APPARATUS FOR GAS CHROMATOGRAPHIC ANALYSIS USING PACKED OR CAPILLARY BORE OPEN TUBULAR COLUMNS AND METHOD OF TESTING

[76] Inventor: Stanley D. Stearns, Box 55603, Houston, Tex. 77055

[21] Appl. No.: 103,450

[22] Filed: Dec. 14, 1979

[51] Int. Cl.³ ............................................. G01N 1/10
[52] U.S. Cl. .............................. 73/863.11; 73/864.81; 73/864.84
[58] Field of Search ......................... 73/422 GC, 23.1; 55/197, 386

[56] References Cited

U.S. PATENT DOCUMENTS

| | | | |
|---|---|---|---|
| 2,757,541 | 8/1956 | Watson et al. | 73/23.1 |
| 3,000,218 | 9/1961 | Marks et al. | 73/23.1 |
| 4,022,065 | 5/1977 | Ramin et al. | 73/422 GC |

*Primary Examiner*—Stephen A. Kreitman

[57] ABSTRACT

The illustrated and preferred embodiment of the present invention is a sample delivery system for packed or open tubular column gas chromatographic apparatus. The apparatus comprises a sample injection valve constructed and arranged to utilize multiple ports wherein a gaseous or liquid sample is injected through a syringe into an injection port, the valve being heated to volatilize the sample which is then temporarily stored in a sample storage loop. The valve apparatus rotates to connect the sample storage loop with an inlet conduit delivering the sample and sweep gas to an exponential dilution flask (EDF). The flask provides an output which delivers a diluted portion of sample with the extent of dilution controlled as a function of time through a second valve assembly. The second valve assembly is switched with a timer to deliver a portion of the sample flow and sweep gas to a capillary bore gas chromatographic apparatus. The first valve may also be used independently as an off-line, septumless inlet for use with packed columns without the dilution stage.

18 Claims, 5 Drawing Figures

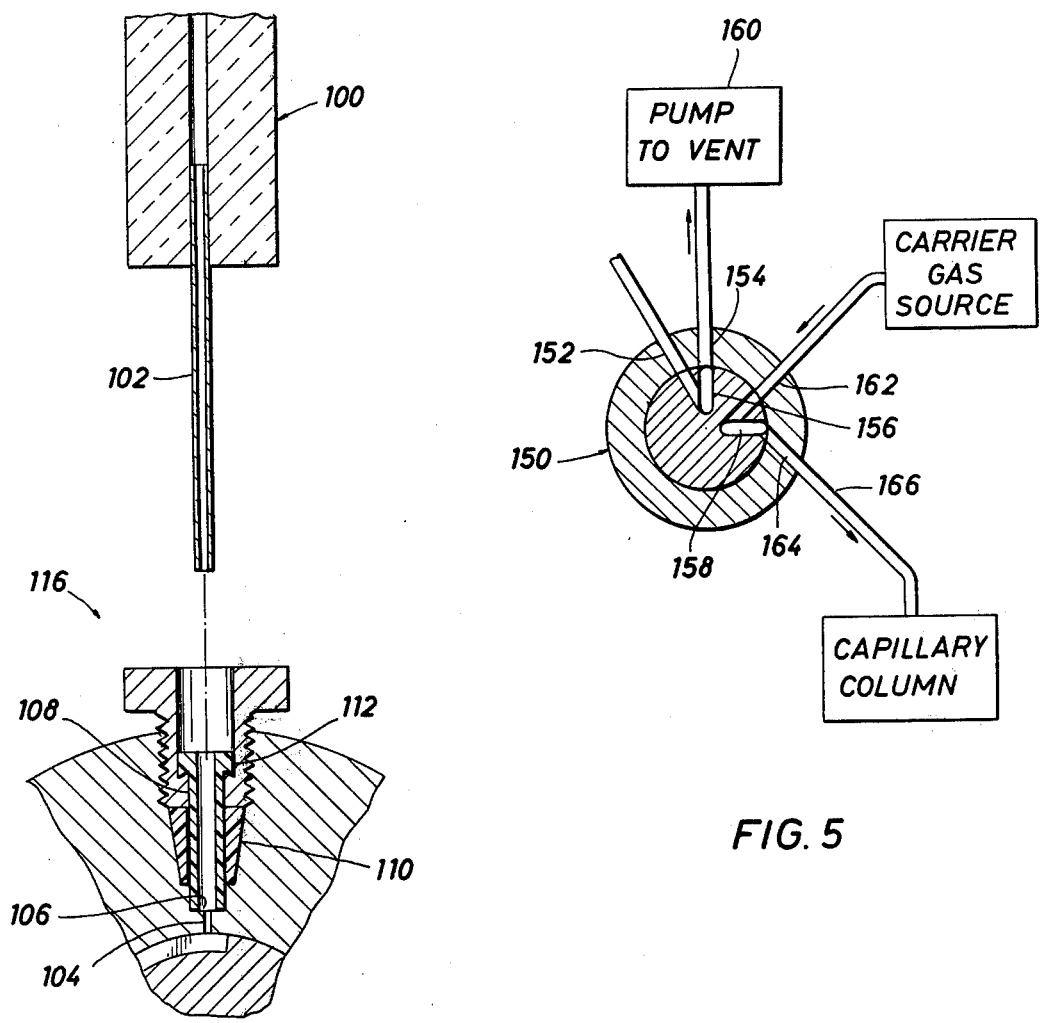

SAMPLE INTRODUCTION APPARATUS FOR GAS CHROMATOGRAPHIC ANALYSIS USING PACKED OR CAPILLARY BORE OPEN TUBULAR COLUMNS AND METHOD OF TESTING

BACKGROUND OF THE DISCLOSURE

Gas chromatographic apparatus utilizing capillary columns is an extremely successful analytical device in the chemical laboratory. Such a device provides very sharp separation between similar compounds, large theoretical plate count and relatively rapid analysis speed. It utilizes a capillary column which has an inside diameter typically less than 0.5 millimeter in diameter. Columns of this sort are extremely valuable in providing very critical separations of similar compounds, but there are great difficulties in preparing the materials for delivery to the column. One difficulty is acquiring a sample sufficiently small to achieve optimal separation of constituent components. In many instances, even where the material to be analyzed is quite small in quantity, the material must be handled in a rather gross fashion in comparison with the size of the necessary sample required for the column. It is common practice to inject an oversized sample into an inlet splitter apparatus. Some sample is always wasted which, in and of itself, is not highly desirable, but, more importantly, it is difficult to know what portion of the excessive or oversized sample has been split into the column and what portion has been wasted. Most importantly, the ratio of splitting varies somewhat with changing molecular weights of sample constituents. Some measure of proportionality must be known in advance so that sample size delivery to the column is properly controlled.

In a typical situation, the size of the sample is only a minute portion of a liter, even as small as 10.0 nanoliters. Nanoliter specimens are so small as to be usually impossible to obtain from a sample delivery system other than through the use of sample splitters and the like.

An early sample splitter utilized a type of passage with a large outlet and a small outlet. The large outlet carries away the bulk of the sample, and, hopefully, the remaining portion passing through the small outlet is precisely controlled so that the capillary column apparatus receives a known percentage of the gross sample delivered to the splitter. There have been other systems for splitless injection which are well documented in the literature. References can be consulted for various known techniques for attempting to obtain a portion of a sample free of bias arising from molecular weight.

There has been some difficulty in achieving analysis of liquids with low boiling point constitutents. The difficulty is not in the testing, per se, but, rather, in the delivery of a specimen of precise volume measure. As an example, if a specimen is maintained in a liquid state under pressure within a syringe prior to injection, a problem later arises in that injection through an elastomeric septum at high temperatures results in fractionation of the sample. Error as a result of fractional vaporization is increased when the light sample constituents partially vaporize and heavier constituents partially remain in liquid or solid form in the syringe needle after injection. This error is randomized by variations in the time the syringe remains in the inlet port.

The present invention is an apparatus which overcomes this by providing a method and an apparatus whereby the injected sample is intentionally vaporized off-line into an open loop before introduction to the separation column. Sample introduction to the gas chromatographic column is then effected either directly or after dilution and an additional sampling stage.

The present invention is uniquely able to handle these problems. Additionally, it simplifies other existing methods by reducing the complexity of preconcentration and solvent stripping techniques, while permitting introduction of smaller, but more quantitative samples.

BRIEF SUMMARY OF THE DISCLOSURE

This disclosure is directed to both a method and apparatus for preparing samples for delivery to capillary column apparatus. The device uses a multiport injection valve assembly having a fixed stator and rotor movable between two positions identified as load and inject positions. A septumless syringe injection port is provided which delivers the specimen into a sample storage loop which has a specified volume which volume is greater than the volume occupied by the fully vaporized sample. A dilution gas is delivered through another inlet port, and the valve is controllably connected with an exponential dilution flask. The rotor is moved to a load position for injection by syringe which injects the sample through the valve. The sample is momentarily heated, vapors are formed and are stored in a loop. The rotor is then moved to the other position whereby the sample storage loop is serially communicated with the exponential dilution flask. The injection valve is optionally heated so that the liquid sample is first volatilized and then delivered along with a dilution gas to the flask. In the flask where the sample is stirred and diluted, the flask provides an outlet flow which meters a controlled quantity of gas over a period of time. The flask outlet flows through a valve operated by a timer which is timed in its switching operation to thereby input a specified quantity of the sample of interest at the selected or desired level of dilution.

The apparatus thus utilizes two valves, the second being operated by a timer controlled to select the particular quantity to be delivered to the capillary column gas chromatograph. Alternately, one dual function valve may replace the two described. Through this arrangement, a beginning sample, whether liquid or gas, can be injected, and any overage in sample size in accommodated by the manner in which the equipment dilutes the sample before column introduction. A precisely measured sample is then delivered to the capillary column gas chromatograph. The first valve is used alone in situations not requiring dilution and also to inject gas samples conventionally.

BRIEF DESCRIPTION OF THE DRAWINGS

So that the manner in which the above recited features, advantages and objects of the invention, as well as others which will become apparent, are attained and can be understood in detail, a more particular description of the invention briefly summarized above may be had by reference to the embodiments thereof illustrated in the appended drawings, which drawings form a part of this specification. It is to be noted, however, that the appended drawings illustrate only typical embodiments of the invention and are not to be considered limiting of its scope, for the invention may admit to other equally effective embodiments.

FIG. 4 is a sectional view of a sample injection valve; and

FIG. 5 is an alternative form of the valves of FIG. 1.

DETAILED DESCRIPTION OF THE DISCLOSED APPARATUS

Figure 1:
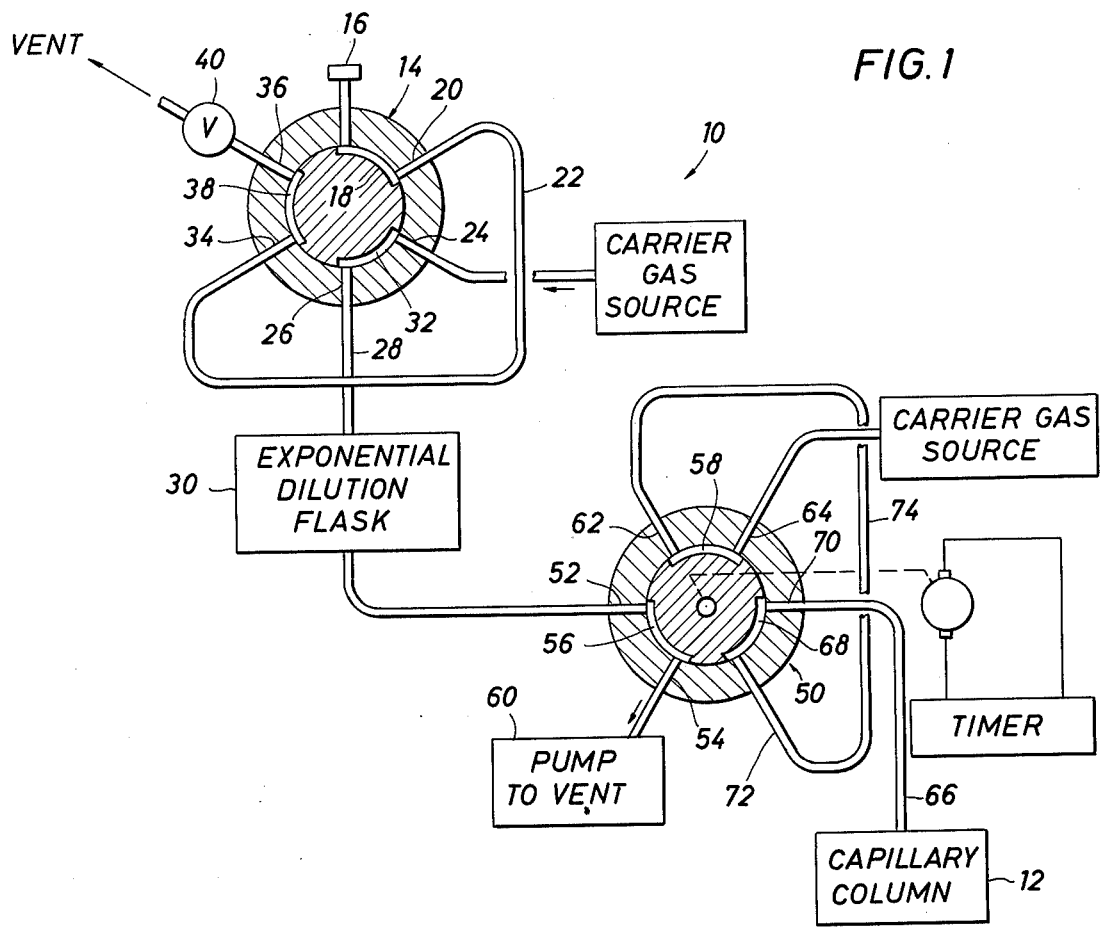
FIG. 1 is a schematic of the system of the present invention showing an arrangement whereby a sample is delivered to a capillary column through the present invention.

Attention is first directed to FIG. 1 where the entire system of the present invention is shown, collectively referred to hereinafter as the sample injection apparatus 0. It cooperates with a capillary column 12. Capillary columns are believed to be well known in the art. As an example, glass capillary columns are furnished by suppliers, such as J & W Scientific, Inc., for use in such detectors. Another source of capillary columns is Chrompack Nederland, N.V. Such columns are additionally marketed by the Perkin Elmer firm.

The present invention works ideally with very small samples, even those below 100.0 nanoliters. The apparatus includes an injection valve 14 which includes six ports in the ideal arrangement. The injection port 16 opens through the surrounding stator and is connected to an internal passage 18 in a movable rotor. It is believed that multiport stator-rotor valves of this sort are well known, and one model of a six-port valve is sold as Model No. CV-6-HTA by Valco Instruments, Inc., Houston, Texas. Another model is CV-6-UHTa-N60, modified as described. While six ports provide an ideal arrangement, the inclusion of more than six ports is not a detriment. The named models are exemplary of construction of the port arrangement, stator and rotor. The injection port 16 connects through the passage 18 to the port 20 which is connected to a sample storage loop 22 having a known or fixed volume. The loop is a storage implement whereby the sample can be received and stored in the loop preparatory to injection to the test instrument. It may be an open tube, or it may be a packed tube to facilitate the discarding of volatile solvents. Loop volume exceeds the vaporized sample volume to enable the sample to be received in the loop. Loading into the loop is accomplished in the manner to be described.

The numeral 24 identifies another externally accessed port which is connected with a sweep gas or dilution gas source. A suitable gas is delivered at a regulated pressure and flow rate to this port. The dilution or carrier gas is normally inert insofar as the process and measuring instrument is concerned. Nitrogen, helium and argon with five percent (5%) methane are gases which may be used. The gas variously identified as a sweep gas, carrier gas or diluent gas. In all instances, the terms refer to various aspects of the common gas used in the system, and the various terms commonly refer to the gas selected for operation. Different gases can be used at different times for a variety of reasons.

The valve includes another port 26 which is adapted to be connected with outlet line 28 which delivers the volatile specimen or sample. Outlet line 28 is connected to an external dilution flask 30 to be described. The ports 24 and 26 are communicated together by a passage 32. The passage 32, as well as the passage 18, is located in the rotor, and they selectively connect between ports as will be described.

The valve 10 incorporates a fifth port 34 which provides a second point of connection for the sample storage loop 22 which is connected to the port 20 as shown in FIG. 1. The sixth port 36 is connected to the port 34 by means of the internal passage 38 which connects to an outlet pressure regulator 40 which, in turn, connects to vent or atmosphere. The pressure regulator can be a restricted orifice passage as one example of acceptable apparatus.

Figure 2:
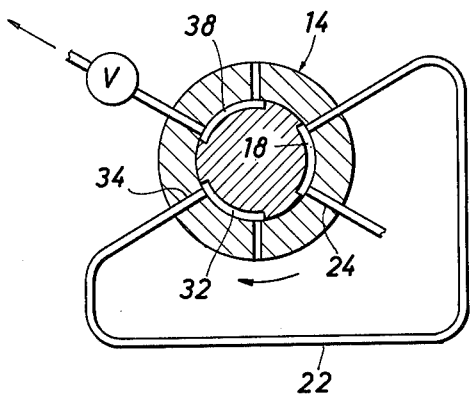
FIG. 2 shows the change in connections achieved on rotation of the rotary valve shown in FIG. 1.

The six ports and the three internal passages (the passages 18, 32 and 38 being in the rotor) connect the ports in the arrangement shown in FIG. 1. This is the load position. Attention is momentarily directed to FIG. 2 of the drawings where it will be observed that the internal passages have been moved by rotation of the rotor in the direction of the arrow. The passage 18 is now between the second and third ports. The passage 32 has been moved to connect the fourth and fifth ports. The passage 38 is now connected between the first and sixth ports. This is the position achieved at the time of delivery of the particular sample. This is the inject position for the sample. Prior to this juncture, the sample is stored in the loop 22 as shown in FIG. 1, which is the load position.

The valve port 16 is constructed in a manner disclosed in U.S. Pat. No. 4,022,065. That patent discloses an injection port liner which seals against syringe needle leakage. The needle abuts a shoulder to limit penetration. The injection port 16 is constructed in the same manner of some resilient material, one suitable material being a cross-linked polymide plastic having a maximum rating of 350° C.

The plastic seal is adjacent to an abutting shoulder opening into a passage as small as 0.010 inch diameter and 0.040 inch long in the stator which ends at the rotor. This defines an offset or error volume of about 45.0 nonoliters, an amount so small that it is inconsequential in most situations, particularly when it contains only gas created from a liquid sample's vaporization. An alternate or enhanced form of the valve injection port 16 is shown in greater detail in FIG. 4.

Loading through the valve is achieved with the position shown in FIG. 1 whereby the sample is injected through the injection port 16 to be stored in the loop 22. The valve is switched from the inject to load position just prior to sample introduction. While in the inject position, the loop is filled with carrier gas. This operation clears the fill port of any previous sample constituents as the hot carrier gas is expelled through the fill port by loop depressurization flowing from the loop 22. The restrictor 40 on the exit port of the valve minimizes back diffusion of atmosphere into the loop and directs most of the loop contents through the fill port prior to injection, a preliminary clearing step. In another embodiment, an auxiliary source of carrier source is fed into the exit port 36 of the valve 14 upstream of the restrictor 40 to completely eliminate atmosphere ingress during and prior to sample loading. In such an embodiment, a pressure relief/venting valve should be provided to permit sample entry at low pressure. After clearing the fill port, the sample in the syringe is injected by positioning the syringe in the fill port, and the syringe plunger is operated to inject the sample through the syringe needle into the valve 14. The liquid sample is heated to vaporize and converts into a larger volume of vapor. The vapor is routed into the loop 22. As the vaporous sample arrives, it displaces carrier gas previously placed in the loop 22. The particular stored specimen in the loop 22 is kept in the loop while the apparatus is in the load position of FIG. 1. Reverse leakage back though the injection port is prevented by leaving the syringe in the injection port. This serves as a stopper or plug, so to speak. The injection of the specimen into the loop 22 is the first step for metering the particular specimen of interest. The specimen is then located in the sample storage loop 22 shown in FIG. 1 preliminary to delivery to the exponential dilution flask (EDF). On switching the valve 14 to the position of FIG. 2, a dilution gas is introduced through the port 24. After switching the rotor, gas is delivered by the internal passage 18 to the sample injection loop 22 behind the sample to force the sample to flow in front of the newly introduced carrier gas through the port 34, the internal passage 32 and the conduit 28 which communicates with the dilution flask 30.

The injection of a volatilized sample into the loop is thus accomplished, and the loop functions mementarily as a storage facility for the sample. The sample gas is flowed in advance to the carrier gas introduced after switching the rotor. The carrier gas thus surrounds the sample, there being a previous carrier gas charge in the loop as a result of initial clearing of the loop before sample injection in the preliminary step of momentarily moving to the load position prior to sample injection.

The apparatus of the present invention particularly operates with liquids or gases. If a gas is injected, the gas is stored in the loop 22. Likewise, if a liquid is injected, it is also received into the loop 22. At this juncture, the method of the present invention teaches the heating of the injection valve 14 to an elevated temperature sufficient to convert the injected liquid sample into a vapor. As the sample passes into the vapor phase, it increases in volume to increase the pressure and forces the carrier gas from the exhaust port. Back pressure is controlled by the restrictor 40. The gaseous sample is then received in the loop 22, stored within the loop without regard to its original phase and is thereafter in a ready location for delivery to the remainder of the equipment.

An example test procedure for liquid injection is worth noting. Assume a liquid sample at room temperature has various components which vaporize at temperatures ranging up to 250° C. In this instance, the syringe and sample (at room temperature) are placed in the port 16. The loop is preliminarily cleared by filling with carrier gas. The port 16 incorporates a seal sleeve made of a material such as Vespel, a cross-linked polyimide, so that heating of the syringe needle occurs, but not so rapidly that the sample is vaporized in the needle. Injection with a syringe forces the sample into the passage emerging from the seal. The sample, on contact with the heated valve body and loop, will vaporize with the lower boiling point materials boiling off first. Since the temperature is greater than the highest boiling constituent of the sample, the sample is completely vaporized.

The sample, along with a flow of dilution gas, flows to the exponential dilution flask 30. This is a device, described well in scientific literature, commonly used to generate, in situ, standards of trace gases. The EDF is not normally usable with a liquid mixture having a wide boiling range since fractionation occurs during sample vaporization and the fast volatilizing fraction will be diluted on a different exponential curve compared to the slower vaporizing fractions, thus making the dilution nonquantitative for the original constituent ratios. The EDF has a sealed chamber having a stirring mechanism in it which mixes incoming gas with the contents of the flask. A flow of gas through the dilution flask carries the sample out of it at a controlled rate. Accordingly, the dilution gas flows through the port 24 from the gas source previously mentioned. Back pressure in the dilution flask 30 is controlled in the manner which will be described. Assuming a flow through the dilution flask and further assuming that uniform stirring is maintained, the gas volume and concentration at the dilution flask outlet is predictable. The concentration as a function of time is given by Equation 1:

$$C_T = C_O e^{(-QT/V)} \tag{1}$$

where
$C_T$ = concentration at time T after dilution;
$C_O$ = initial concentration;
$Q$ = flow rate;
$V$ = volume of flask; and
$T$ = elapsed time after injection.

Figure 3:
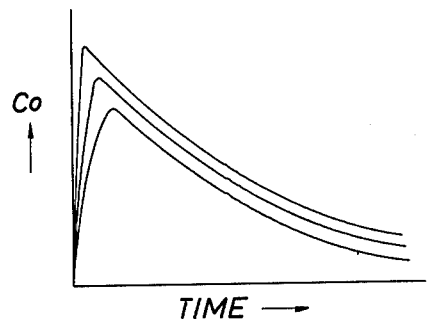
FIG. 3 is a timing versus concentration chart showing dilution of the sample of interest.

From the foregoing, it will be observed that the peak gas concentration occurs at the beginning time. FIG. 3 shows this in graphic form. Multiple curves are included to show the effect of different gas concentrations at the flask inlet. The beginning or initial concentrations may have different peak values, but they all decay in a family of curves approximately given by the family of curves shown at FIG. 3. There is a small time lag for transfer from inlet to outlet on introduction of a gas sample into the flask. The outlet concentration jumps rapidly to a maximum value and decays in the manner charted at FIG. 3. The equation given above and the family of curves shown in FIG. 3 presume a fixed or regulated back pressure. The peak shape consistently has the exponential decay form on limiting pressure variations. Controlling the pressure in the EDF and downstream sample volume, either by restricting the outflow for increased pressure or connection to a vacuum pump for reduced pressure, permits varying the volume of sample to be injected into the downstream chromatographic column. The combination of a small volume downstream sample valve with a reduced outlet pressure permits injection of the sample into as little as one theoretical plate volume, even when that one plate is represented by 1.0 millimeter of tubing of 0.010 inch tubing.

Returning now to FIG. 1 of the drawings, a second valve 50 is a multiport valve having a fixed stator and movable rotor. The ports are the same as valve 14, although a valve with different ports is acceptable. A duplicate valve can be used as a convenience. In any case, the numeral 52 identifies the first port which is the inlet port. The outlet flow from the dilution flask 30 is through the port 52. The numeral 54 identifies a second port which is connected by an internal conduit 56 to the port 52. They collectively connect with an optional pump 60 which vents the gas flow. The pump 60 provides a regulated and controlled flow of gas communicated with the dilution flask 30 through the valve mechanism 50. The pump 60 can pull a vacuum to thereby decrease the size of the sample taken by the loop, but this factor is far less important than the regulation of the pressure at the flask 30 and the valve 50. The flow through the flask 30 is thus regulated by the pump.

The apparatus further includes connection for the capillary column gas chromatograph 12. The valve 50 incorporates two additional internal passages 58 and 68 which connect to additional ports 62, 64, 70 and 72.

Ports 62 and 72 are connected by a conduit 74 which may be a calibrated loop or flow line. When the rotor is switched, the flow of the sample of interest is introduced into the port 52, the passage 56, the port 62, the conduit 74 and held there momentarily. The port 64 connects with the conduit 66 to the capillary column 12 for capillary separation.

The valve 50 is switched in timed fashion. To this end, it can be automated to deliver sample. The valve 50 is operated at a time and for an interval to obtain a sample of desired concentration. Referring to FIG. 3 of the drawings, suppose that a point on the uppermost curve describes the sample concentration of interest. Suppose further that the valve 50 is switched 2.0 seconds after switching the valve 10 to the inject position to obtain a required sample concentration. The duration of the interval between the switching of the valve 14 to the inject position and the valve 50 to the inject position determines the dilution of the sample delivered to the capillary. The calibration of the sample occurs through the dilution accomplished in the sample upstream of the capillary 12 and, in particular, the precise dilution achieved through the exponential dilution flask 30. The output of the flask 30 makes available to the sample valve 50 a mechanism whereby the gas is aptly delivered in timely fashion. In other words, the user can obtain a calculated dilution of the original sample. Because a sample is mixed in the dilution flask, the concentration of sample which is delivered through the injection valve 50 is precisely controlled.

The injection valve 14 is preferably manufactured with an even number of ports, and six is the ideal number. Moreover, the valve includes the fixed stator which surrounds the rotatable rotor having the internal passages. The entire apparatus is sealed at the injection port against leaks to atmosphere as better known in the sectional view of FIG. 4. The entire apparatus can be heated to several hundred degrees C. as an assistance in volatilizing the sample using Vespel and stainless steel building materials.

The sample injection valve of the present invention is adapted to be used as a means for vaporizing the sample. A typical sample will be in the form of a liquid and is composed of several different substances. Each constituent of the sample may have a different volatilization point and a different vapor pressure. This then, of necessity, constrains the sample to volatilize at a wide temperature range dependent on the nature of its constituents. As the sample is volatilized, the heavier constituents which volatilize the slowest may, in fact, be left behind and thereby distort the mix of the constituents delivered to the test apparatus. As a result, it is highly desirable that all the constituents be volatilized as close together in time so that the constituent parts are mixed in the sample even in the vaporous state. By contrast, if this were not the case, the heavier or more slowly volatilized constituents might be left behind after the lighter constituents of the sample are driven off as gaseous vapors. This would distort test data obtained from the sample.

The present invention, therefore, contemplates and teaches the use of a sample injection valve which is formed of a stator and rotor. The two components are made of stainless steel or some other material capable of handling increased or elevated temperatures, typically up to about 350° C. This, therefore, additionally requires that the valve be constructed and designed to operate at such elevated temperatures and to seal against leakage at high temperatures. Just as important, it is then desirable to maintain a very small offset, if any, between the injection port 16 and the rotor passage 18. The passage which is to be located at the end of the needle inserted into the injection port 16 is thus very small. A small passage is in the vicinity of about 0.010 inch in diameter and about 0.040 inch in length to thereby reduce the offset cavity to relatively samll nanoliter range. An example is shown in FIG. 4.

Attention is directed to FIG. 4 which disclosed an injection port in detail. The numeral 100 identifies a syringe having a fairly long needle 102 of relatively thin wall construction. A small gauge needle will suffice. The needle 102 is several centimeters long, approximately 3.0 to 5.0 centimeters long. The injection port 116 in the stator body includes a small bottom located passage 104. This is approximately 0.010 inches in diameter and 0.040 inches in length. It opens to the rotor passages, and the passage 104 represents the waste volume. The passage 104 is centered in a shoulder area 106 which limits needle penetration into the injection port 116. The shoulder also registers a two-part sleeve made of an insulative plastic such as Vespel. The sleeve is an insulator which limits heat transfer into the needle 102. The needle contacts only the shoulder 106 and the surrounding sleeve. The sleeve is made of two pieces, an inner liner 108 and an outer, tapered, hollow grommet 110. The sleeve 108 has an upper surrounding shoulder 112. The shoulder 110 locks inside a counterbored passage in a hollow, threaded fitting 114. The fitting has an external thread to join to the stator, the depth of thread limiting penetration into the stator.

The injection port 116 does not contact the needle with metal except at the end of the needle by the shoulder 106. The plastic sleeve is the only surface contacting the needle to form a seal against leakage. At worst, only the tip of the long needle is heated. Heat transfer is primarily from the metal shoulder 106 and is not from the sleeve 108. The sleeve is relatively poor heat transfer material which does not heat the needle sufficiently to heat the body of the syringe and the sample. The sample remains cool and does not volatilize until injection, even if the needle rests in the stator for several minutes.

The inject port construction assures that the sample vaporizes as it is heated which occurs in or beyond the narrow passage 104. This assures that the specimen is fully switched into the sample loop, leaving only the passage 104 as a wasted volume. The waste volume is only a few nanoliters, reducing error to a minimum.

The last factor of reduced error comes into play at the time that the injection syringe is inserted into the port. On insertion, the syringe, which is typically at room temperature and holding a liquid sample typically at room temperature, is seated in the injection port 16 with a needle which bottoms out adjacent to the internal offset passage. Heat from the heated sample injection valve impinges on the syringe at the needle and can flow, to a limited extent, back through the needle into the body of the syringe. However, the syringe normally has a mass, compared to the slowly heated needle, that does not initiate substantial volatilization in the syringe needle. The present invention is superior to previously used septum injection systems. This is particularly the case even when a syringe is left in the injection port without injection for a substantial period of time. In any case, when the syringe is operated to inject the sample, the sample is heated rather quickly and is vaporized to force its way along the passage 18 and through the port 20. At this point, the syringe is substantially empty, but it is held in the injection port to plug the port against backflow of vapors out through the port. As the vapors are created from the liquid sample, the expansion which inevitably occurs intitiates a flow into the sample storage loop.

The opposite end of the sample storage loop is provided as shown in FIG. 1 with a back pressure restrictor or pressure regulator valve 40. It permits clearing the sample storage loop 22 of gas in the loop as the sample expands. Inert materials of construction should be used to minimize destruction of reactive components of the sample.

The sample injection valve can be connected directly by connecting the line 28 to a gas chromatographic column and then to a detector. This can be used where the exponential dilution flask is not required as would be the case for a packed column of larger internal diameter than the capillary columns described herein. It will be recalled that the exponential dilution flask cuts down the size of the sample for a capillary column which is keyed to operate with a very small volume.

It is desirable that the sweep gas from the port 24 be flushed through the port 24 and through the sample storage loop (see FIG. 2) so that the loop 22 is filled with the sweep gas in advance. Then, the valve is operated to the load position (shown in FIG. 1) at which time the pressurized gas in the sample storage loop will vent through the syringe port 16. The syringe port 16 has a small and known offset at the very bottom where the tip of the needle is registered, and this offset was described before, but the offset, itself, connects with a sleeve (see FIG. 4). The sleeve is preferably up to about 0.750 inch in length. The area and length of the sleeve should be minimized to limit heat transfer to the syringe needle and, thus, the sample within. It serves as a receptacle for the syringe placed in the port, and, as the sweep gas flows out through the port 16 prior to syringe insertion, reverse purging action occurs at the lower portions of the syringe port whereby carrier gas is expelled, and the syringe port is cleared, ready to receive the sample to be volatilized. After this step, the only two gases in the sample loop are the sweep gas, which was there before the sample was inserted, and the vapors formed by the sample, itself. Moreover, external air does not enter the system as long as the inserted syringe is held in the port with the tip placed at the bottom of the passage. Use of a large volume loop with the small flows permitted via the fill port and vent 40 makes possible insertion of the syringe needle during loop depressurization. This facility minimizes the introduction of atmosphere into the sample loop along with the sample. This is important since oxygen in contact with a hot sample may cause partial degradation of some portion of the sample. Both valves 14 and 50 can conveniently be identical, the models named serving as the preferred forms. A ten-port model is also made by the same source, and it can also be used for both valves.

FIG. 5 discloses a four-port valve 150 having a stator and rotor. The rotor includes a pair of internal passages and is movable between two positions. The four ports are the inlet port 152 connected to a vent port 154 via an internal connective passage 156. This passage has a specified volume and receives and stores a sample volume when positioned as shown in FIG. 5. A second internal passage 158 connects between ports 162 and 164. The port 154 optionally connects to a vacuum pump placing a regulated back pressure on the system, while the port 162 is an input for carrier gas. The port 164 connects to a conduit 166 for the capillary column. This combination supplies carrier gas to the column except on switching the rotor.

The valve 150 does not have a sample storage loop. Rather, it uses the sample storage cavity 156 as a temporary storage chamber for the gaseous sample, having a fixed or known volume. The loop is omitted, reducing the complexity of the valve 150 to four ports. Momentary switching of the rotor moves the captured sample into a flow path between the carrier gas source leading to the capillary column. This easily delivers the sample for testing.

One variation in this invention is made by placing the valve 14 in a thermostat controlled oven to stabilize temperature. A temperature is selected above the highest boiling point suspected for the sample. Another variation is made by placing a motor or other drive means on the rotor for switching the rotor for a timed interval.

The foregoing is directed to the preferred and illustrated embodiment, but the scope thereof is determined by the claims which follow.

I claim:

1. A sample injection valve having a relatively fixed stator and a movable rotor having a plurality of ports in the stator, the ports comprising a syringe injection port, a sample loop storage connecting port, a second sample storage loop connecting port, a dilution gas introduction port, a back pressure vent port and an outlet port, there being three internal passages within said rotor means which are selectively moved to connect with pairs of said ports and wherein said sample injection port is adapted to receive a syringe for injection a sample thereinto and further wherein said stator and rotor are made of a material which can be elevated to a temperature sufficient to convert the injected sample into a gas by heating thereof wherein the injected sample gas is then received and stored in the sample injection loop;
    wherein said syringe injection port terminates at a relatively small offset volume and serially connects with one of the internal passages within said rotor;
    a source of a dilution gas which is introduced through the dilution gas port and is conducted by one of the internal passages to fill the sample loop connected to the sample loop ports;
    wherein said sample injection valve is switched to communicate said sample injection storage loop with said syringe injection port prior to insertion of a syringe such that the sample injection port is filled from the internal passage towards the exterior by the dilution gas;
    wherein the sample from the syringe is a liquid which liquid is heated by the sample injection valve on delivery from the syringe to vaporize and flow into the sample storage loop in a gaseous state; and
    wherein said sample storage loop is sized to receive the entirety of the vaporized sample.

2. The apparatus of claim 1 wherein said back pressure vent port is adapted to be connected to flow restrictor means which means regulates pressure in the sample storage loop to control gas flow from the sample stoage loop prior to loading the sample.

3. The apparatus of claim 1 wherein said syringe injection port comprises an internal shoulder abutting and limiting entry of a syringe needle and a surrounding seal means about a passage extending to said shoulder where said shoulder terminates a passage for delivery of sample to said internal passage and including an exponential dilution flask connected to said outlet port.

4. The apparatus of claim 1 including means for controllably flowing a dilution gas into said sample loop to be flowed through said injection port.

5. A method of obtaining a sample of suitable small size from a liquid specimen which forms an oversized sample for testing in chromatographic apparatus which utilizes a small sample wherein the method comprises the steps of:
(a) injecting a liquid sample into a sample storage means;
(b) vaporizing the sample to form a gas in the sample storage means;
(c) introducing the stored gas sample from the sample storage means into an exponential dilution flask along with a dilution gas for mixing therein;
(d) removing a selected portion of the diluted sample from the dilution flask; and
(e) controllably delivering the portion of the dilute sample flowing from the dilution flask into a gas chromatograph column.

6. The method of claim 5 wherein the step of injecting a liquid sample into the sample storage means occurs after introducing carrier gas through a dilution gas port into the sample storage means.

7. The method of claim 5 wherein the step of vaporizing the sample includes the step of preheating a syringe receiving means connected to said sample storage means prior to receiving a syringe having the liquid sample therein and wherein the sample injection receiving means is preheated to above a specified temperature so that selected constituents in the injected liquid sample will be vaporized.

8. The method of claim 5 wherein the exponential dilution flask is continuously stirred prior to introduction of the stored gas sample and wherein the stored gas sample flows into the flask with the dilution gas so that both are introduced through a single point of entry into the flask.

9. The method of claim 8 wherein the flow from the dilution flask is passed through a sample injection valve which has load and inject positions and wherein the valve is switched at some time after the stored gas sample has been introduced into the dilution flask and further wherein the valve is thereafter closed and further including the method step of timing the delivery of carrier gas for a capillary column for gas chromatographic analysis with the closing of the valve such that the sample with the dilution gas is first introduced into the capillary column and a carrier gas is introduced thereafter.

10. The method of claim 5 including the step of regulating the pressure of the flow of sample from the dilution flask.

11. A method of obtaining gas sample from a liquid specimen for testing in chromatographic apparatus which comprises the steps of:

(a) loading a liquid sample into a syringe;
(b) injecting the liquid sample into a sample injection port of a sample injection valve which valve is heated to a temperature sufficiently high to vaporize the sample constitutents;
(c) wherein the valve includes a connected sample storage means and the vaporized sample is received therein;
(d) preventing escape of the sample injected in the sample injection port until vaporization is complete;
(e) operating the valve to isolate the sample injection port from the sample storage means; and
(f) diluting the vaporized sample by controllably mixing the sample in a selected ratio with an inert dilution gas.

12. The method of claim 11 wherein the step of injecting a liquid sample into the sample injection port occurs after introducing a carrier gas into the sample storage means to clear the sample storage means prior to introduction of the sample.

13. The method of claim 11 including the step of mixing the vaporized sample by introducing the vaporized sample into a mixing flask with a dilution gas and mixing therein, and extracting diluted vaporized sample from the flask for a selected time interval.

14. The method of claim 11 including the step of first sweeping the sample storage means with a carrier gas prior to injection of the sample.

15. The method of claim 11 wherein the valve is preheated to a temperature sufficient to volatilize all selected constituents in the sample.

16. The method of claim 11 wherein the sample is loaded as a liquid into a syringe at room temperature and is injected to form a vapor and is stored in a sample loop serving as the sample storage means, and wherein the sample storage means is isolated after injection, and, thereafter, the sample is forced from the storage loop by introducing a carrier gas thereinto.

17. Sample delivery apparatus comprising:
(b) an exponential dilution flask having an inlet and an outlet;
(b) inlet valve means
(1) connected an at outlet to said flask inlet;
(2) having an inlet port on said valve means for receiving a sample;
(3) said valve comprising an operable valve element to controllably flow a sample from said inlet port to said outlet and then to said flask;
(c) outlet valve means
(1) having an inlet connected to said flask outlet; and
(2) having a valve element to controllably flow a sample through the inlet and to an outlet.

18. The apparatus of claim 17 wherein inlet valve means includes an inlet for a carrier gas selectively flowing through said inlet valve means to said dilution flask means.

* * * * *